United States Patent
Bueno Harto et al.

(10) Patent No.: US 6,913,731 B2
(45) Date of Patent: Jul. 5, 2005

(54) OXYGEN PROBE

(75) Inventors: José Manuel Bueno Harto, Madrid (ES); Francisco Javier Perosanz Lopez, Madrid (ES)

(73) Assignee: Union Fenosa Generacion, S.A., Madrid (ES)

( * ) Notice: Subject to any disclaimer, the term of this patent is extended or adjusted under 35 U.S.C. 154(b) by 475 days.

(21) Appl. No.: 10/072,627

(22) Filed: Feb. 8, 2002

(65) Prior Publication Data

US 2002/0144559 A1 Oct. 10, 2002

Related U.S. Application Data

(63) Continuation of application No. PCT/ES00/00309, filed on Aug. 4, 2000.

(30) Foreign Application Priority Data

Aug. 10, 1999 (ES) .............................................. P 9901836

(51) Int. Cl.[7] ........................ G01N 21/00; G01N 27/00; G01N 31/00; G01N 33/00; G01N 7/00

(52) U.S. Cl. ............................ 422/83; 422/94; 422/95; 422/96; 422/97; 422/98; 436/43; 436/127; 436/136; 436/137; 436/138; 436/149; 73/1.01; 73/1.02; 73/23.2; 73/23.31; 73/23.32; 204/193; 204/194; 204/424; 204/427; 204/428; 204/429; 204/431

(58) Field of Search ............................... 422/83, 94, 95, 422/96, 97, 98; 436/43, 127, 136, 137, 138, 149; 73/1.01, 1.02, 23.2, 23.31, 23.32; 204/193, 194, 424, 427, 428, 429, 431

(56) References Cited

U.S. PATENT DOCUMENTS

| | | | | |
|---|---|---|---|---|
| 4,193,857 A | * | 3/1980 | Bannister et al. | 204/428 |
| 4,980,042 A | * | 12/1990 | Shiomi et al. | 204/427 |
| 5,049,255 A | | 9/1991 | Wolfe et al. | |
| 5,073,247 A | | 12/1991 | Weyl | |
| 5,112,456 A | * | 5/1992 | Worrell et al. | 205/783.5 |
| 5,596,134 A | * | 1/1997 | Phillippi et al. | 73/19.07 |

FOREIGN PATENT DOCUMENTS

| | | |
|---|---|---|
| EP | 0 702 229 | 3/1996 |
| EP | 0 899 562 | 3/1999 |
| ES | 2 074 521 | 10/1991 |
| JP | 11-190717 | 7/1999 |

* cited by examiner

*Primary Examiner*—Jill Warden
*Assistant Examiner*—Brian Sines
(74) *Attorney, Agent, or Firm*—Katten Muchin Rosenman

(57) ABSTRACT

Intended for application on ducts through which flow a fluid at a high temperature, and particularly at a high pressure, comprising two bodies (4) and (8) which axially screw onto each other, one body (4) provided with a threaded neck (5) for attachment to the orifice of duct wall (3), which body (4) houses within it sensor element (2) of the probe which is thus placed inside the duct, with second body (8) screwed onto first body (4) and exerting on sensor element (2) the pressure required to secure it in its housing, with second body (8) further provided with an axial orifice through which passes a metallic tube (9) open to the exterior and which is provided with a metallic washer (10), soldered to said tube (9), which is separated from second body (8) by an electrically insulating washer (12).

1 Claim, 1 Drawing Sheet

OXYGEN PROBE

CROSS REFERENCE TO RELATED APPLICATION

This application is a continuation of International PCT Application No. PCT/ES00/00309 filed on Aug. 4, 2000.

OBJECT OF THE INVENTION

The invention relates to a probe which is sensitive to the amount of oxygen present in a fluid, with operation conditions requiring said probe to withstand high temperatures and, particularly, high pressures.

The object of the invention is to provide an oxygen probe which operates using the oxygen concentration battery principle, in which probe can be established a potential difference measurable on either side of an ionic conducting tube (sensor element) immersed in the fluid, constructed such that it can be used in conditions of extreme temperature and pressure, as those corresponding to water-steam circuits in nuclear and thermal plants.

BACKGROUND OF THE INVENTION

A sensor is a measurement device placed in the vicinity of an enclosure in which flow or are contained gases, liquids or whichever element to be measured, and which responds in a known and predictable manner to fluctuations in the measured variable. Generally speaking, a sensor can be divided into two parts:

1) Probe
2) Power and/or signal conversion-adaptation electronics.

The probe, which is the element placed in the vicinity of the area to be measured, can in turn be divided into:

The sensor element, which generates a change in a property which can be measured as a function of the variation of the measurement variable.

Support element(s), whose function is to mechanically secure the sensor element to the area where the measurement is performed; in addition, in certain cases it may serve as an thermal or electronic insulator to ensure suitable working conditions for the probe.

The probe also requires complementary electronics which can translate the signal arriving from said probe into a comprehensible figure expressed in appropriate units.

In order to determine $O_2$ and $CO_2$ levels, or those of any other components of combustion, probes are known which are placed in the exhaust ducts of vehicles powered by combustion engines.

In this sense can be cited European Patent EP-0448817, particularly conceived for application for exhaust pipe gases, where existent pressures are low, so that the mechanical design of the probe object of this European Patent does not allow its use in ducts which simultaneously have high temperatures and high pressures.

An oxygen sensing unit is described in document U.S. Pat. No. 5,049,255, which comprises a first and a second metallic bodies axially screwed onto each other. This sensing unit is specially designed for sensing oxygen in automotive exhausts, but would not perform efficiently in ducts under conditions of extreme temperature and pressure.

DESCRIPTION OF THE INVENTION

The probe object of this invention has a simple and effective design, and is embodied with a simple and sturdy construction, so that it can withstand extreme temperature and pressure conditions.

More specifically, the probe of the invention comprises two metallic bodies which are axially screwed onto each other, the first of which is in turn screwed onto an opening provided for such purpose in the wall of the duct where the probe is to be employed. In order to prevent leaks of fluid from the pressurised area a gasket is placed between the enclosure wall and the rear stop of maximum penetration of the threaded neck of the aforementioned metallic body, creating a hermetic seal.

As the measurement principles is based on a potential difference the ends between which said potential difference, that is, the internal and external parts of the sensor element must be electrically insulated.

The second body screwed inside the previous one is meant to keep the sensor element in its housing, applying the pressure required to attain a hermetic seal between the first metallic body and the atmosphere. This seal must be achieved by means of a metallic deformable washer to maintain electrical continuity between the external and internal parts of the sensor element and the first metallic body.

The second body is provided with an axial orifice through which passes a metallic tube which has two purposes:

Providing communication between the inside of the sensor element of the probe and the surrounding atmosphere.

Continuing the electrical contact from the internal face of the sensor element to the outside of the probe in order to measure the aforementioned potential difference.

In order to achieve the latter, said metallic tube is provided with a metal washer welded to it which makes electrical contact with the inner wall of the sensor element. This tube must be insulated in turn from the second body by means of a protective sheath which prevents short circuit of the signal.

This requires that the pressure applied by the sensor element on the first body take place through an interposed electrically insulating washer between the second body and the metal washer of the tube, so that the required electrical insulation is maintained.

DESCRIPTION OF THE DRAWINGS

These and further characteristics and advantages of the present invention will be better understood in view of the accompanying drawing of a preferred embodiment of the invention, where for purposes of illustration only a longitudinal sectional view is shown of the probe set as applied on the duct.

PREFERRED EMBODIMENT OF THE INVENTION

Figure 1:
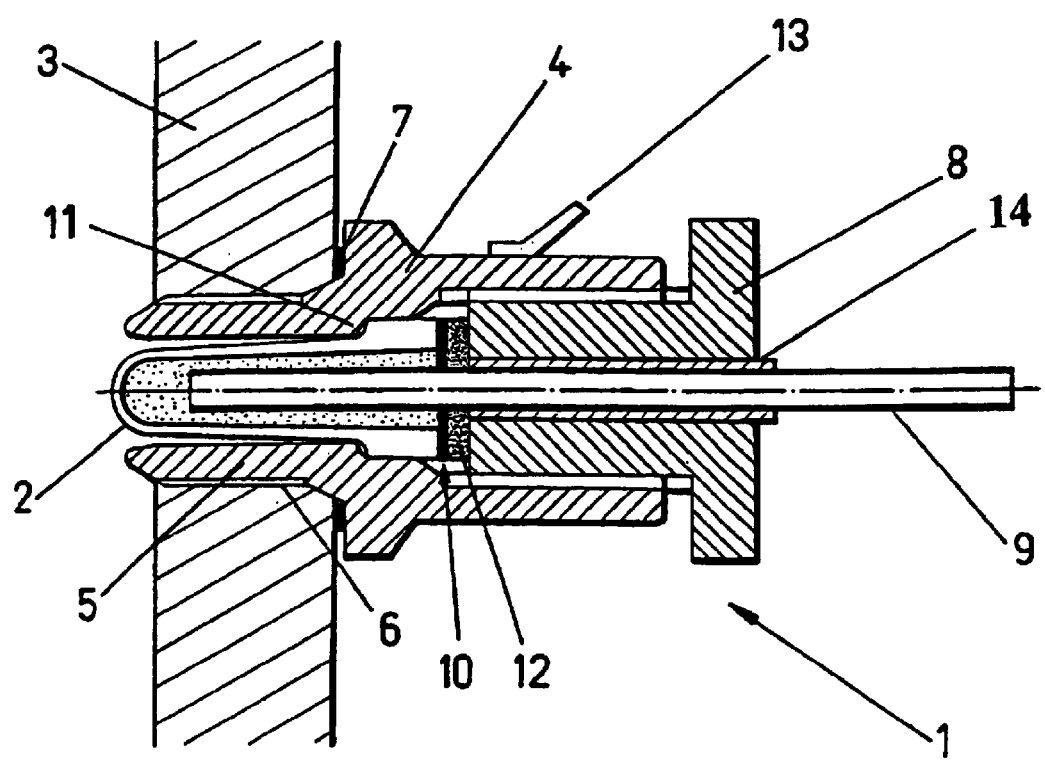

As may be seen in the aforementioned figure (FIG. 1), probe (1) and specifically its sensor element labelled (2), is meant to measure the oxygen in a fluid which flows through a duct with a wall labelled (3), inside which there exist high temperatures and pressures.

The sensor element of probe (2) is placed inside a body (4) which is mounted through a neck (5) onto an orifice provided for such purpose in duct wall (3), which mounting is achieved by threading (6).

The maximum penetration of body (4) is limited in its screwing on the orifice of duct wall (3) by its front area which stops against the outer surface of said wall (3), with the particular characteristic that the assembly is made hermetic by the interposition of a gasket (7).

Additionally, on its inside body (4) is provided with a seat for the rear area of the probe's sensor element (2).

The structure is complemented by a second body (8) which is screwed axially onto the inside of body (4), such that in its axial motion as it is screwed inside body (4) said second body (8) presses against the sensor element (2) of the probe in its housing.

Body (8) is provided with an axial concentric orifice for passage of a metal tube (9) which contacts the inner metallic surface of probe sensor element (2) through a metallic washer (10) soldered to said tube (9), establishing the connection required for measurement.

The seal between external part of sensor element (2) and the surrounding atmosphere is achieved by means of a deformable metallic washer (11). The pressure exerted by second body (8) on sensor element (2) in order to secure it in its housing takes place with an electrically insulating washer (12) interposed between the second body (8) and the metallic washer (10) soldered to metal tube (9), which electrically contacts the inner part of sensor element (2).

The potential difference established is measured between metal tube (9) and first metal body (4). In order to aid the electrical connection between metallic body (4) and the signal transmission wire, an electric connector (13) may be welded to first body (4).

Lastly, metallic tube (9) is insulated from second body (8) by a protective sheath (14) which prevents short circuit of the signal.

We claim:

1. Oxygen probe, meant for application in ducts through which flows a fluid and in which there exist extreme temperature and, particularly, extreme pressures, with a sensor element (2) of said probe housed in a mounting structure of the probe for coupling onto a pressurised duct or enclosure with the assistance of a gasket (7) which provides a hermetic mount for the probe, said mounting structure comprising a first metallic body (4) and a second metallic body (8) screwed axially inside the first body (4) pressing onto the sensor element (2), wherein a gasket (7) is interposed between said first body (4) and the duct characterized in that the first body (4) is provided with a neck (5) for mounting by a thread (6) on an orifice provided for such purpose on wall (3) of the duct or pressurised enclosure, said neck (5) surrounding the sensor element (2) and extending internally from the wall (3), the first body (4) having an internal seat for stopping the sensor element (2) in cooperation with a rear area provided in the sensor element (2) and with a deformable metallic washer to obtain a hermetic seal, the second body (8) being provided with an axial concentric passage wherein a metallic tube (9) and a protective sheath (14) are placed, the protective sheath (14) interposed therein providing insulation, said metallic tube (9) having soldered a metallic washer (10) which is in electric contact with the sensor element (2).

* * * * *